US012774493B2

(12) United States Patent
Miller et al.

(10) Patent No.: US 12,774,493 B2
(45) Date of Patent: Oct. 27, 2026

(54) METHODS FOR CHEMICAL CLEAVAGE OF SURFACE-BOUND POLYNUCLEOTIDES

(71) Applicant: Illumina, Inc., San Diego, CA (US)

(72) Inventors: Oliver Miller, Cambridge (GB); Pietro Marafini, Cambridge (GB); Alix Kwasniewska, Cambridge (GB)

(73) Assignee: Illumina, Inc., San Diego, CA (US)

( * ) Notice: Subject to any disclaimer, the term of this patent is extended or adjusted under 35 U.S.C. 154(b) by 781 days.

(21) Appl. No.: 18/191,299

(22) Filed: Mar. 28, 2023

(65) Prior Publication Data

US 2023/0313294 A1 Oct. 5, 2023

Related U.S. Application Data

(60) Provisional application No. 63/325,394, filed on Mar. 30, 2022.

(51) Int. Cl.
*C12Q 1/68* (2018.01)
*C12Q 1/6874* (2018.01)
*C07H 21/04* (2006.01)

(52) U.S. Cl.
CPC ........... *C12Q 1/6874* (2013.01); *C07H 21/04* (2013.01)

(58) Field of Classification Search
CPC .............................. C12Q 1/6874; C07H 21/04
See application file for complete search history.

(56) References Cited

U.S. PATENT DOCUMENTS

| | | | |
|---|---|---|---|
| 5,302,509 | A | 4/1994 | Cheeseman |
| 6,172,218 | B1 | 1/2001 | Brenner |
| 6,465,178 | B2 | 10/2002 | Chappa et al. |
| 2009/0088327 | A1 | 4/2009 | Rigatti et al. |
| 2009/0118128 | A1 | 5/2009 | Liu et al. |
| 2012/0309634 | A1 | 12/2012 | Rigatti et al. |
| 2014/0079923 | A1 | 3/2014 | George et al. |
| 2020/0131484 | A1 | 4/2020 | Golynskiy et al. |
| 2020/0181587 | A1 | 6/2020 | Klausing et al. |
| 2024/0141427 | A1 | 5/2024 | Golynskiy et al. |

FOREIGN PATENT DOCUMENTS

| | | |
|---|---|---|
| WO | WO 98/44151 | 10/1998 |
| WO | WO 98/44152 | 10/1998 |
| WO | WO 00/06770 | 2/2000 |
| WO | WO 00/18957 | 4/2000 |
| WO | WO 00/31148 | 6/2000 |
| WO | WO 01/01143 | 1/2001 |
| WO | WO 01/57248 | 8/2001 |
| WO | WO 02/012566 | 2/2002 |

(Continued)

OTHER PUBLICATIONS

Margulies, Sep. 15, 2005, Genome sequencing in microfabricated high-density picolitre reactors, Nature, 437:376-380.

(Continued)

*Primary Examiner* — Jezia Riley
(74) *Attorney, Agent, or Firm* — Illumina, Inc.

(57) ABSTRACT

Embodiments of the present disclosure relate to modified extension primers for use in generating clustered polynucleotides for sequencing by synthesis. In particular, the disclosure relates to methods of chemically linearizing clustered polynucleotides in preparation for sequencing by cleavage of one or more strands of double-stranded polynucleotides immobilized on a solid support by a periodate salt.

20 Claims, 2 Drawing Sheets

Specification includes a Sequence Listing.

(56) References Cited

FOREIGN PATENT DOCUMENTS

| | | |
|---|---|---|
| WO | WO 03/014392 | 2/2003 |
| WO | WO 05/024010 | 3/2005 |
| WO | WO 05/047301 | 5/2005 |
| WO | WO 05/065814 | 7/2005 |
| WO | WO 06/120433 | 11/2006 |
| WO | WO 07/010251 | 1/2007 |
| WO | WO 00/53812 | 9/2020 |

OTHER PUBLICATIONS

Scheit, K. H. (1980). *Nucleotide analogs: Synthesis and biological function*. New York: John Wiley & Sons, TOC, 5 pages.
Schendure et al., Sep. 9, 2005, Accurate multiplex polony sequencing of an evolved bacterial genome, Science, 309(5741):1728-1732.
Uhlman et al., Jun. 1990, Antisense oligonucleotides: a new therapeutic principle, Chemical Reviews, 90(4):543-584.

SEQUENCE LISTING

```
Sequence total quantity: 25
SEQ ID NO: 1            moltype = DNA  length = 29
FEATURE                 Location/Qualifiers
source                  1..29
                        mol_type = other DNA
                        organism = synthetic construct
```

-continued

```
misc_feature           23
                       note = n is a deoxyuridine
SEQUENCE: 1
aatgatacgg cgaccaccga ganctacac                                    29

SEQ ID NO: 2           moltype = DNA  length = 24
FEATURE                Location/Qualifiers
source                 1..24
                       mol_type = other DNA
                       organism = synthetic construct
misc_feature           22
                       note = n is a 8-oxo-guanine
SEQUENCE: 2
caagcagaag acggcatacg anat                                         24

SEQ ID NO: 3           moltype = DNA  length = 39
FEATURE                Location/Qualifiers
misc_feature           1
                       note = 5 prime alkyne
source                 1..39
                       mol_type = other DNA
                       organism = synthetic construct
misc_feature           33
                       note = n is a deoxyuridine
SEQUENCE: 3
tttttttttt aatgatacgg cgaccaccga ganctacac                         39

SEQ ID NO: 4           moltype = DNA  length = 34
FEATURE                Location/Qualifiers
misc_feature           32
                       note = n is a 8-oxo-guanine
misc_feature           1
                       note = 5 prime alkyne
source                 1..34
                       mol_type = other DNA
                       organism = synthetic construct
SEQUENCE: 4
tttttttttt caagcagaag acggcatacg anat                              34

SEQ ID NO: 5           moltype = DNA  length = 20
FEATURE                Location/Qualifiers
source                 1..20
                       mol_type = other DNA
                       organism = synthetic construct
SEQUENCE: 5
aatgatacgg cgaccaccga                                              20

SEQ ID NO: 6           moltype = DNA  length = 21
FEATURE                Location/Qualifiers
source                 1..21
                       mol_type = other DNA
                       organism = synthetic construct
SEQUENCE: 6
caagcagaag acggcatacg a                                            21

SEQ ID NO: 7           moltype = DNA  length = 29
FEATURE                Location/Qualifiers
misc_feature           23
                       note = n is a vinyl substituted T nucleoside
source                 1..29
                       mol_type = other DNA
                       organism = synthetic construct
SEQUENCE: 7
aatgatacgg cgaccaccga ganctacac                                    29

SEQ ID NO: 8           moltype = DNA  length = 27
FEATURE                Location/Qualifiers
misc_feature           1..3
                       note = diol linker subject to chemical cleavage
source                 1..27
                       mol_type = other DNA
                       organism = synthetic construct
SEQUENCE: 8
nnncaagcag aagacggcat acgagat                                      27

SEQ ID NO: 9           moltype = DNA  length = 35
FEATURE                Location/Qualifiers
misc_feature           29
                       note = a vinyl substituted T nucleoside
```

-continued

```
misc_feature            1
                        note = 5 prime alkyne
source                  1..35
                        mol_type = other DNA
                        organism = synthetic construct
SEQUENCE: 9
tttttaatg atacggcgac caccgaganc tacac                           35

SEQ ID NO: 10           moltype = DNA  length = 33
FEATURE                 Location/Qualifiers
misc_feature            7..9
                        note = diol linker subject to chemical cleavage
misc_feature            1
                        note = 5 prime alkyne
source                  1..33
                        mol_type = other DNA
                        organism = synthetic construct
SEQUENCE: 10
ttttttnnnc aagcagaaga cggcatacga gat                            33

SEQ ID NO: 11           moltype = DNA  length = 33
FEATURE                 Location/Qualifiers
misc_feature            2..4
                        note = diol linker subject to chemical cleavage
misc_feature            1
                        note = 5 prime alkyne
source                  1..33
                        mol_type = other DNA
                        organism = synthetic construct
SEQUENCE: 11
tnnnttttttc aagcagaaga cggcatacga gat                           33

SEQ ID NO: 12           moltype = DNA  length = 32
FEATURE                 Location/Qualifiers
misc_feature            2..3
                        note = diol linker subject to chemical cleavage
misc_feature            1
                        note = 5 prime alkyne
source                  1..32
                        mol_type = other DNA
                        organism = synthetic construct
SEQUENCE: 12
tnnttttca agcagaagac ggcatacgag at                              32

SEQ ID NO: 13           moltype = DNA  length = 31
FEATURE                 Location/Qualifiers
misc_feature            2
                        note = diol linker subject to chemical cleavage
misc_feature            1
                        note = 5 prime alkyne
source                  1..31
                        mol_type = other DNA
                        organism = synthetic construct
SEQUENCE: 13
tnttttcaa gcagaagacg gcatacgaga t                               31

SEQ ID NO: 14           moltype = DNA  length = 33
FEATURE                 Location/Qualifiers
misc_feature            1..3
                        note = diol linker subject to chemical cleavage
misc_feature            1
                        note = Alkyne on terminal end
source                  1..33
                        mol_type = other DNA
                        organism = synthetic construct
SEQUENCE: 14
nnnttttttc aagcagaaga cggcatacga gat                            33

SEQ ID NO: 15           moltype = DNA  length = 32
FEATURE                 Location/Qualifiers
misc_feature            1..2
                        note = diol linker subject to chemical cleavage
misc_feature            1
                        note = Alkyne on terminal end
source                  1..32
                        mol_type = other DNA
                        organism = synthetic construct
SEQUENCE: 15
nnttttttca agcagaagac ggcatacgag at                             32
```

-continued

SEQ ID NO: 16 moltype = DNA length = 31
FEATURE Location/Qualifiers
misc_feature 1
note = diol linker subject to chemical cleavage
misc_feature 1
note = Alkyne on terminal end
source 1..31
mol_type = other DNA
organism = synthetic construct
SEQUENCE: 16
nttttttcaa gcagaagacg gcatacgaga t 31

SEQ ID NO: 17 moltype = DNA length = 33
FEATURE Location/Qualifiers
misc_feature 3..5
note = diol linker subject to chemical cleavage
misc_feature 1
note = 5 prime alkyne
source 1..33
mol_type = other DNA
organism = synthetic construct
SEQUENCE: 17
ttnnntttc aagcagaaga cggcatacga gat 33

SEQ ID NO: 18 moltype = DNA length = 32
FEATURE Location/Qualifiers
misc_feature 3..4
note = diol linker subject to chemical cleavage
misc_feature 1
note = 5 prime alkyne
source 1..32
mol_type = other DNA
organism = synthetic construct
SEQUENCE: 18
ttnnttttca agcagaagac ggcatacgag at 32

SEQ ID NO: 19 moltype = DNA length = 31
FEATURE Location/Qualifiers
misc_feature 3
note = diol linker subject to chemical cleavage
misc_feature 1
note = 5 prime alkyne
source 1..31
mol_type = other DNA
organism = synthetic construct
SEQUENCE: 19
ttnttttcaa gcagaagacg gcatacgaga t 31

SEQ ID NO: 20 moltype = DNA length = 33
FEATURE Location/Qualifiers
misc_feature 4..6
note = diol linker subject to chemical cleavage
misc_feature 1
note = 5 prime alkyne
source 1..33
mol_type = other DNA
organism = synthetic construct
SEQUENCE: 20
tttnnntttc aagcagaaga cggcatacga gat 33

SEQ ID NO: 21 moltype = DNA length = 32
FEATURE Location/Qualifiers
misc_feature 4..5
note = diol linker subject to chemical cleavage
misc_feature 1
note = 5 prime alkyne
source 1..32
mol_type = other DNA
organism = synthetic construct
SEQUENCE: 21
tttnntttca agcagaagac ggcatacgag at 32

SEQ ID NO: 22 moltype = DNA length = 31
FEATURE Location/Qualifiers
misc_feature 4
note = diol linker subject to chemical cleavage
misc_feature 1
note = 5 prime alkyne -continued

```
source                  1..31
                        mol_type = other DNA
                        organism = synthetic construct
SEQUENCE: 22
tttntttcaa gcagaagacg gcatacgaga t                                31

SEQ ID NO: 23           moltype = DNA  length = 33
FEATURE                 Location/Qualifiers
misc_feature            5..7
                        note = diol linker subject to chemical cleavage
misc_feature            1
                        note = 5 prime alkyne
source                  1..33
                        mol_type = other DNA
                        organism = synthetic construct
SEQUENCE: 23
ttttnnnttc aagcagaaga cggcatacga gat                              33

SEQ ID NO: 24           moltype = DNA  length = 32
FEATURE                 Location/Qualifiers
misc_feature            5..6
                        note = diol linker subject to chemical cleavage
misc_feature            1
                        note = 5 prime alkyne
source                  1..32
                        mol_type = other DNA
                        organism = synthetic construct
SEQUENCE: 24
ttttnnttca agcagaagac ggcatacgag at                               32

SEQ ID NO: 25           moltype = DNA  length = 31
FEATURE                 Location/Qualifiers
misc_feature            5
                        note = diol linker subject to chemical cleavage
misc_feature            1
                        note = 5 primer alkyne
source                  1..31
                        mol_type = other DNA
                        organism = synthetic construct
SEQUENCE: 25
ttttnttcaa gcagaagacg gcatacgaga t                                31
```

METHODS FOR CHEMICAL CLEAVAGE OF SURFACE-BOUND POLYNUCLEOTIDES

CROSS-REFERENCE TO RELATED APPLICATION

This application claims the benefit of priority to U.S. Provisional Application No. 63/325,394, filed Mar. 30, 2022, the content of which is incorporated by reference in its entirety.

FIELD

Embodiments of the present disclosure relate to compositions and methods of chemical linearization of double-stranded polynucleotides for sequencing-by-synthesis (SBS).

REFERENCE TO SEQUENCE LISTING

The present application is being filed along with a Sequence Listing in electronic format. The Sequence Listing is provided as a file entitled Sequence_listing_ ILLINC_ 715A.xml created Mar. 24, 2023, which is 38.7 Kb in size. The information in the electronic format of the Sequence Listing is incorporated herein by reference in its entirety.

BACKGROUND

Various nucleic acid sequencing methods are known in the art. U.S. Pat. No. 5,302,509 describes a method for sequencing a polynucleotide template that involves performing multiple extension reactions using a DNA polymerase or DNA ligase to successively incorporate labelled polynucleotides complementary to a template strand. In such a SBS reaction, a new polynucleotide strand based-paired to the template strand is built up in the 5' to 3' direction by successive incorporation of individual nucleotides complementary to the template strand. The substrate nucleoside triphosphates used in the sequencing reaction are labelled at the 3' position with different 3' labels, permitting determination of the identity of the incorporated nucleotide as successive nucleotides are added.

In order to maximize the throughput of nucleic acid sequencing reactions it is advantageous to be able to sequence multiple template molecules in parallel. Parallel processing of multiple templates can be achieved with the use of nucleic acid array technology. These arrays typically consist of a high-density matrix of polynucleotides immobilized onto a solid support material.

Various methods for fabrication of arrays of immobilized nucleic assays have been described in the art. WO 98/44151 and WO 00/18957 both describe methods of nucleic acid amplification which allow amplification products to be immobilized on a solid support in order to form arrays comprised of clusters or "colonies" formed from a plurality of identical immobilized polynucleotide strands and a plurality of identical immobilized complementary strands. Arrays of this type are referred to herein as "clustered arrays." The nucleic acid molecules present in DNA colonies on the clustered arrays prepared according to these methods can provide templates for sequencing reactions, for example as described in WO 98/44152. The products of solid-phase amplification reactions such as those described in WO 98/44151 and WO 00/18957 are so-called "bridged" structures formed by annealing of pairs of immobilized polynucleotide strands and immobilized complementary strands, both strands being attached to the solid support at the 5' end. In order to provide more suitable templates for nucleic acid sequencing, it is preferred to remove substantially all or at least a portion of one of the immobilized strands in the "bridged" structure in order to generate a template which is at least partially single-stranded. The portion of the template which is single-stranded will thus be available for hybridization to a sequencing primer. The process of removing all or a portion of one immobilized strand in a "bridged" double-stranded nucleic acid structure is referred to as "linearization." There are various ways for linearization, including but not limited to enzymatic cleavage, photochemical cleavage, or chemical cleavage. Non-limiting examples of linearization methods are disclosed in PCT Publication No. WO 2007/010251 and U.S. Patent Publication No. 2009/0088327, and in U.S. Patent Publication No. 2009/0118128, which are incorporated by reference in their entireties.

Enzymatic methods are known to facilitate efficient site-specific cleavage of oligonucleotides or polynucleotides to linearize double stranded DNA clusters and to deprotect surface-bound primers. Currently, enzymes have been extensively used in both of these types of reactions in various sequencing applications. However, there are certain issues with the enzymatic approaches, including enzyme stability, costs of enzyme production, specific storage and handling requirements, variations in enzyme activity, and high background intensity in sequencing reading. Therefore, there exists a need to develop alternative linearization and deprotection methods for effective DNA sequencing. However, there are many limitations on the reaction types that can be applied to linearization steps in this context, as the reagents, conditions, and byproducts (a) must be compatible with up- and downstream reactions, including oligonucleotide hybridization and denature, primer PCR extension, and DNA synthesis, (b) must display good stability under acidic, basic, and oxidative conditions, (c) must effect a rapid and clean chemical reaction, and (d) must not interfere with nucleotide detection methods. The present disclosure describes compositions for chemical cleavage of double stranded DNA that is an effective alternative that meets the requirements described above.

SUMMARY

One aspect of the present disclosure relates to a method of linearizing a plurality of immobilized double-stranded polynucleotides, comprising:

- contacting a solid support comprising a plurality of immobilized double-stranded polynucleotides with a periodate salt composition, wherein each double-stranded polynucleotides comprises a first strand and a second strand, the first strand and the second strand are immobilized to the solid support at their 5' ends, and the second strand comprises a P17' primer sequence, and wherein the P17' primer sequence comprises a cleavage site having one or more diol linkers; and
- cleaving one or more second strands at the cleavage site with the periodate salt and generating one or more cleaved second polynucleotides. In some embodiment, the P17' primer sequence comprises SEQ ID NO. 11.

Another aspect of the present disclosure relates to a method of sequencing polynucleotides, comprising:

- contacting a palladium catalyst with a solid support comprising a plurality of immobilized double-stranded polynucleotides, wherein each double-stranded polynucleotides comprises a first strand and a second strand, the first strand and the second strand are immobilized to the solid support at their 5' ends, wherein the first strand comprises a first cleavage site comprising a vinyl moiety, the second strand comprises a P17' primer sequence, and the P17' primer sequence comprises a second cleavage site comprising one or more diol linkers;

cleaving one or more first strands at the first cleavage site with the palladium catalyst, and generating one or more cleaved first polynucleotides and cleaved immobilized first strands;

sequencing the immobilized second strands;

resynthesizing derivative first strands that are complementary to the second strands;

contacting a periodate salt composition with one or more second strands to cleave the second strands at the second cleavage sites, and generating one or more cleaved second polynucleotides and cleaved immobilized second strands; and sequencing the immobilized derivative first strands. In some embodiment, the P17' primer sequence comprises SEQ ID NO. 11.

Another aspect of the present disclosure relates to a method of reducing sequencing by synthesis error rate, comprising:

contacting a solid support comprising a plurality of immobilized double-stranded polynucleotides with a first cleavage reagent, wherein each double-stranded polynucleotides comprises a first strand and a second strand, the first strand and the second strand are immobilized to the solid support at their 5' ends, wherein the first strand comprises a first cleavage site capable of being cleaved by the first cleavage reagent, the second strand comprises a P17' primer sequence, and the P17' primer sequence comprises a second cleavage site comprising one or more diol linkers;

cleaving one or more first strands at the first cleavage site with the first cleavage reagent, and generating one or more cleaved first polynucleotides and cleaved immobilized first strands;

performing a first run of sequencing of the immobilized second strands;

resynthesizing derivative first strands that are complementary to the second strands;

contacting a periodate salt composition with one or more second strands to cleave the second strands at the second cleavage sites, and generating one or more cleaved second polynucleotides and cleaved immobilized second strands; and performing a second round of sequencing of the immobilized derivative first strands; wherein the method results in at least about 5% reduction in the second round of sequencing error rate relative to methods wherein the second strand comprises a P17 primer sequence. In some embodiment, the P17' primer sequence comprises SEQ ID NO. 11.

A further aspect of the present disclosure relates to a solid support comprising:

a plurality of immobilized first extension primers; and a plurality of immobilized second extension primers;

wherein both the first extension primers and the second extension primers are immobilized at their 5' ends;

the first extension primer comprises a first cleavage site; and the second extension primer comprises a P17' primer sequence comprising one or more diol linkers. In some embodiment, the P17' primer sequence comprises SEQ ID NO. 11.

DETAILED DESCRIPTION

Figure 1:
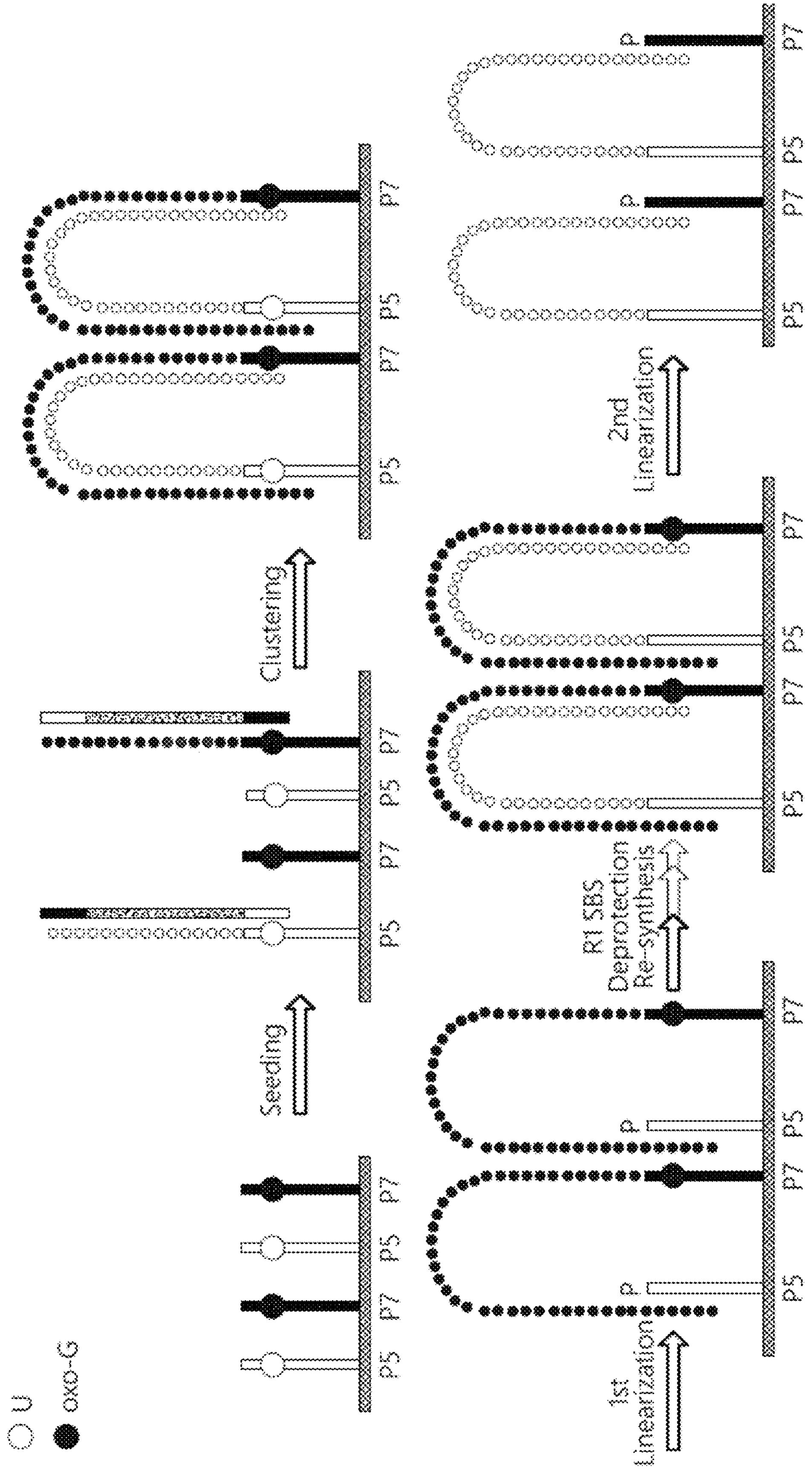
FIG. 1 illustrates an embodiment of a workflow of the Illumina's Sequencing-by-Synthesis (SBS) chemistry using enzymatic linearization.

Non-enzymatic chemical linearization strategies are an attractive alternative for cleaving the bridged double-stranded polynucleotide structures ahead of each sequencing read. In particular, chemicals can often be stored for prolonged periods at room temperature and are relatively inexpensive compared to enzymes. Furthermore, chemical compositions may further be shipped and/or stored in a lyophilized form and be reconstituted into an aqueous solution prior to use. If required, one or both strands of the double-stranded nucleic acid molecule may include one or more non-nucleotide chemical moieties and/or non-natural nucleotides and/or non-natural backbone linkages in order to permit a chemical cleavage reaction at a specific cleavage site, preferably a pre-determined cleavage site.

Diol linker units based on phosphoramidite chemistry suitable for incorporation into polynucleotide chains are commercially available from Fidelity Systems, Inc. (Gaithersburg, MD, USA). One or more diol units may be incorporated into a polynucleotide using standard methods for automated chemical DNA synthesis. In order to position the diol linker at an optimum distance from the solid support one or more spacer molecules may be included between the diol linker and the site of attachment to the solid support. The spacer molecule may be a non-nucleotide chemical moiety. Suitable spacer units based on phosphoramidite chemistry for use in conjunction with diol linkers are also supplied by Fidelity Systems, Inc. The diol linker is cleaved by treatment with a "cleaving agent", which can be any substance which promotes cleavage of the diol. The preferred cleaving agent is periodate, preferably aqueous sodium periodate ($NaIO_4$). Following treatment with the cleaving agent (e.g., periodate) to cleave the diol, the cleaved product may be treated with a "capping agent" in order to neutralize reactive species generated in the cleavage reaction. Suitable capping agents for this purpose include amines, such as ethanolamine. Advantageously, the capping agent (e.g., ethanolamine) may be included in a mixture with the cleaving agent (e.g., periodate) so that reactive species are capped as soon as they are formed. In one non-limiting embodiment, one strand of the double-stranded nucleic acid molecule may include a diol linkage which permits cleavage by treatment with periodate (e.g., sodium periodate). The diol linkage may be positioned at a cleavage site, the precise location of which may be selected by the user. It will be appreciated that more than one diol could be included at the cleavage site.

The combination of a diol linkage and a periodate salt to achieve cleavage of one strand of a double-stranded nucleic acid molecule is preferred for linearization of nucleic acid molecules on solid supported polyacrylamide hydrogels because treatment with periodate is compatible with nucleic acid integrity and with the chemistry of the hydrogel surface. However, sodium periodate aqueous solution tends to form a precipitate after several freeze/thaw cycles. The formation of the precipitate may result in decreased linearization rate or efficiency.

Embodiments of the present disclosure relates to methods of linearizing double-stranded polynucleotides extended from extension primers comprising diol linkers, and the subsequent sequencing application. The diol linkers may be cleaved by a periodate salt composition comprising an ionic liquid additive to substantially reduce or prevent the formation of precipitate after repeated freeze/thaw cycles.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. The use of the term “including” as well as other forms, such as “include”, “includes,” and “included,” is not limiting. The use of the term “having” as well as other forms, such as “have”, “has,” and “had,” is not limiting. As used in this specification, whether in a transitional phrase or in the body of the claim, the terms “comprise(s)” and “comprising” are to be interpreted as having an open-ended meaning. That is, the above terms are to be interpreted synonymously with the phrases “having at least” or “including at least.” For example, when used in the context of a process, the term “comprising” means that the process includes at least the recited steps, but may include additional steps. When used in the context of a compound, composition, or device, the term “comprising” means that the compound, composition, or device includes at least the recited features or components, but may also include additional features or components.

As used herein, the term “covalently attached” or “covalently bonded” refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction.

As used herein, the term “extension primer” refers to an oligonucleotide or polynucleotide immobilized on a solid support, where the oligonucleotide or polynucleotide is capable of specifically binding to a sequence of a target single strand nucleic acid molecule. After a hybridization process, the oligonucleotide or polynucleotide is extended to comprise sequence that is complimentary to the target nucleic acid molecule. In some instances, the term “extension primer” is used interchangeably with “amplification primer” or “clustering primer.” The extension primer described herein may include P5/P7, P15/P17, P5/P17', or P15/P17' primers. Specific examples of suitable primers include P5 and/or P7 primers, which are used on the surface of commercial flow cells sold by Illumina, Inc., for sequencing on HISEQ™, HISEQX™, MISEQ™, MISEQDX™ MINISEQ™, NEXTSEQ™, NEXTSEQDX™, NOVASEQ™, GENOME ANALYZER™, ISEQ™ and other instrument platforms. Certain primer sequences are described in U.S. Pat. Pub. No. 2011/0059865 A1, which is incorporated herein by reference. The standard P5 and P7 primer sequences for the paired-end sequencing comprise the following:

```
P5: paired end 5'→3'
SEQ ID NO. 1: AATGATACGGCGACCACCGAGAUCTACAC

P7: paired end 5'→3'
SEQ ID NO. 2: CAAGCAGAAGACGGCATACGAG*AT
```

where G* is 8-oxo-guanine.

Optionally, one or both of the P5 and P7 primers can include a poly T tail. The poly T tail is generally located at the 5' end of the above sequences, but in some cases can be located at the 3' end. The poly T sequence can include any number of T nucleotides, for example, from 2 to 20.

The standard P5 and P7 primer sequences used on a PAZAM coated flow cell with a poly-T spacer comprise the following:

```
P5 primer with poly-T spacer:
SEQ ID NO. 3: 5'-alkyne-TTTTTTTTTTAATGATACGGCGACCACCGAGAUCTACAC

P7 primer with poly-T spacer:
SEQ ID NO. 4: 5'-alkyne-TTTTTTTTTTCAAGCAGAAGACGGCATACGAG*AT
```

where G* is 8-oxo-guanine.

Additional primer sequences include a set of P5 and P7 primers for single read SBS:

```
P5: single read: 5'→3'
SEQ ID NO. 5: AATGATACGGCGACCACCGA

P7: single read 5'→3'
SEQ ID NO. 6: CAAGCAGAAGACGGCATACGA
```

As used herein, when the standard P5/P7 primers or oligos are modified to incorporate a first or second cleavage site that is capable of undergoing chemical cleavage, for example, by a Pd complex or a periodate salt, the modification of the P5/P7 primers may refer to the replacement or substitution of an existing nucleotide (or nucleoside) in the P5/P7 sequence with a different chemical entity, for example, a modified nucleotide or nucleoside analogue with specific functionality to enable site-specific chemical cleavage. The modification may also refer to the insertion of a new chemical entity into the existing P5/P7 sequence, where the new chemical entity is capable of undergoing site-specific chemical cleavage. In some embodiments, the modified P5 primer is referred to as the P15 primer. The P7 primer may be modified in two ways: the first is referred to as the P17 primer, while the second is referred to as the P17' primer. The P15 and P17 primers are disclosed in U.S. Publication No. 2019/0352327, which is incorporated by reference in its entirety. In particular, the P15, P17, and P17' primers may comprise the following:

P15: 5'→3'
SEQ ID NO. 7: AATGATACGGCGACCACCGAGAT*CTACAC

P17 primer 5'→3'
SEQ ID NO. 8: YYYCAAGCAGAAGACGGCATACGAGAT

P15 primer 5'→3'
SEQ ID NO. 9: 5'-alkyne-TTTTTTAATGATACGGCGACCACCGAGAT*CTACAC

P17 primer 5'→3'
SEQ ID NO. 10: 5'-alkyne-TTTTTTYYYCAAGCAGAAGACGGCATACGAGAT

P17' primer 5'→3'
SEQ ID NO. 11: 5'-alkyne-TYYYTTTTTCAAGCAGAAGACGGCATACGAGAT SEQ ID NO. 12: 5'-alkyne-TYYTTTTTCAAGCAGAAGACGGCATACGAGAT SEQ ID NO. 13: 5'-alkyne-TYTTTTTCAAGCAGAAGACGGCATACGAGAT SEQ ID NO. 14: 5'-alkyne-YYYTTTTTTCAAGCAGAAGACGGCATACGAGAT SEQ ID NO. 15: 5'-alkyne-YYTTTTTTCAAGCAGAAGACGGCATACGAGAT SEQ ID NO. 16: 5'-alkyne-YTTTTTTCAAGCAGAAGACGGCATACGAGAT SEQ ID NO. 17: 5'-alkyne-TTYYYTTTTCAAGCAGAAGACGGCATACGAGAT SEQ ID NO. 18: 5'-alkyne-TTYYTTTTCAAGCAGAAGACGGCATACGAGAT SEQ ID NO. 19: 5'-alkyne-TTYTTTTCAAGCAGAAGACGGCATACGAGAT SEQ ID NO. 20: 5'-alkyne-TTTYYYTTTCAAGCAGAAGACGGCATACGAGAT SEQ ID NO. 21: 5'-alkyne-TTTYYTTTCAAGCAGAAGACGGCATACGAGAT SEQ ID NO. 22: 5'-alkyne-TTTYTTTCAAGCAGAAGACGGCATACGAGAT SEQ ID NO. 23: 5'-alkyne-TTTTYYYTTCAAGCAGAAGACGGCATACGAGAT SEQ ID NO. 24: 5'-alkyne-TTTTYYTTCAAGCAGAAGACGGCATACGAGAT SEQ ID NO. 25: 5'-alkyne-TTTTYTTCAAGCAGAAGACGGCATACGAGAT where T* is a vinyl substituted T nucleoside; and Y is a diol linker subject to chemical cleavage, for example, by oxidation with a reagent such as periodate, as disclosed in U.S. Publication No. 2012/0309634, which is incorporated by reference in its entirety. In some embodiments, the diol linker comprises a Formula (I) or (Ia) as described herein. In some embodiments, the vinyl substituted T nucleoside comprises a Formula (II) as described herein. In further embodiments, the 5'-alkyne moiety is a 5'-hexynyl.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g., found in deoxyribonucleic acid (DNA)) or a ribose sugar (e.g., found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells or the like.

As used herein, the term "polynucleotide" refers to nucleic acids in general, including DNA (e.g., genomic DNA or cDNA), RNA (e.g., mRNA), synthetic oligonucleotides and synthetic nucleic acid analogs. Polynucleotides may include natural or non-natural bases, or combinations thereof and natural or non-natural backbone linkages, e.g., phosphorothioates, PNA or 2'-O-methyl-RNA, or combinations thereof. In some instances, the term "polynucleotide," "oligonucleotide," or "oligo" are used interchangeably.

The term "cleavage site" as used herein refers to a position on the polynucleotide sequence where a portion of the polynucleotide may be removed by a cleavage reaction. The position of the cleavage site is preferably pre-determined, meaning the location where the cleavage reaction happens is determined in advance, as opposed to cleavage at a random site where the location of which is not known in advance.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (e.g., acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers. Particularly useful solid supports for some embodiments are components of a flow cell or located within a flow cell apparatus. The solid support may have a planar surface, for example, a flow cell, or a non-planar surface, for example, a bead.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

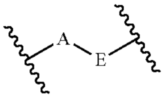

includes the substituent being oriented such that the A is attached at the leftmost attachment point of the molecule as well as the case in which A is attached at the rightmost attachment point of the molecule.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxy group that is present in ribose. The nitrogen containing heterocyclic base can be purine or pyrimidine base. Purine bases include adenine (A) and guanine (G), and modified derivatives or analogs thereof, such as 7-deaza adenine or 7-deaza guanine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, deazapurine, 7-deaza adenine, 7-deaza guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analog" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

Methods of Chemical Linearization with a Periodate Salt

One aspect of the present disclosure relates to a method of linearizing a plurality of immobilized double-stranded polynucleotides, comprising:

contacting a solid support comprising a plurality of immobilized double-stranded polynucleotides with a periodate salt composition, wherein each double-stranded polynucleotides comprises a first strand and a second strand, the first strand and the second strand are immobilized to the solid support at their 5' ends, and the second strand comprises a P17' primer sequence, and wherein the P17' primer sequence comprises a cleavage site having one or more diol linkers; and cleaving one or more second strands at the cleavage site with the periodate salt to generate one or more cleaved second polynucleotides.

In some embodiments of the periodate linearization method described herein, the method further comprises removing the cleaved second polynucleotides from the solid support.

In some embodiments, the cleavage site of the second strand comprises at least two diol linker moieties. In further embodiment, the cleavage site comprises three diol linker moieties. In some embodiments, the diol linker moiety comprises a structure of Formula (I):

(I)

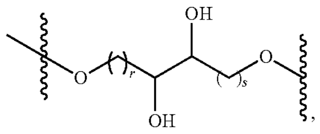

wherein r is 2, 3, 4, 5, or 6; and s is 2, 3, 4, 5, or 6. In further embodiments, the diol linker comprises or has the structure:

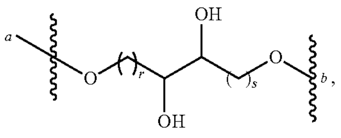

where the "a" oxygen is the 3' hydroxyl oxygen of a first nucleotide; and the "b" oxygen is the 5' hydroxyl oxygen of a second nucleotide. In one embodiment, the diol linker comprises a structure of Formula (Ia):

(Ia)

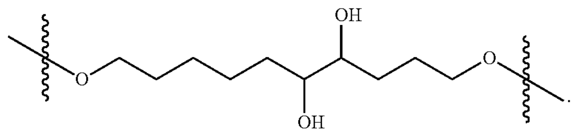

In a further embodiment, the diol linker comprises or has a structure of

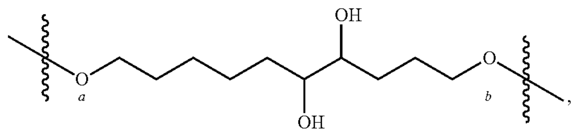 [SMILES: *OCCCCCC(O)C(O)CCCO*]

where the "a" oxygen is the 3' hydroxyl oxygen of a first nucleotide; and the "b" oxygen is the 5' hydroxyl oxygen of a second nucleotide.

In some embodiments of the periodate linearization method described herein, the second strands are extended from second extension primers immobilized to the solid support, and wherein the second extension primer comprises the P17' primer sequence. In one embodiment, the second extension primer is a P17' primer.

In any embodiments of the periodate linearization method described herein, the P17' primer sequence comprises SEQ ID NO. 11.

Methods of Sequencing

FIG. 1 describes an embodiment of a standard workflow of the Illumina SBS chemistry. First, a solid support comprising a plurality of P5/P7 primers immobilized on the surface of the solid support is provided. Each of the P5 and the P7 primers has a cleavage site within the sequence. In one embodiment, the cleavage site on the P5 primer is a deoxyuridine (U). In one embodiment, the cleavage site on the P7 primer is an 8-oxo-guanine nucleotide (oxo-G). A set of target DNA molecules to be sequenced is hybridized to the immobilized P5/P7 primers. After hybridization, the original target DNA molecules are removed, leaving only the complementary copies of the extended polynucleotides containing the P5/P7 primers. This step is also known as a "seeding" step. Then, the extended P5/P7 polynucleotides are amplified through a process called the "bridge amplification," forming double-stranded clusters with both strands being attached to the solid support at the 5' end. After the "clustering" step, the first linearization is performed to remove a portion of the extended polynucleotides containing the P5 primer. In one embodiment, such removal is facilitated by an enzymatic cleavage reaction using an enzyme USER to cleave the U position on the P5 primer (first linearization step). After a first round of SBS (Read 1), a resynthesis is carried out to form the double-stranded polynucleotides again. Then, a second linearization is performed to remove a portion of the extended polynucleotides containing the P7 primer. In one embodiment, such removal is facilitated by an enzymatic cleavage reaction using enzyme FPG to cleave the oxo-G position of the P7 primer. Then a second round of SBS is carried out (Read 2) to sequence the target DNA.

Alternatively, either or both of the first linearization and the second linearization steps may use a chemical cleavage method instead of enzymatic cleavage. For example, the P5 primer may be replaced by the P15 primer and the P7 primer may be replaced by the P17 primer and/or the P17' primer. In this case, the first linearization step may be achieved by a chemical cleavage linearization using a Pd catalyst described herein. The second linearization step may also be achieved by a chemical cleavage linearization using the periodate composition (e.g., sodium periodate) described herein.

Alternatively, the solid support may comprise P5/P17 primers and/or P5/P17' primers. In this case, the first linearization step may be achieved by an enzymatic linearization using USER. The second linearization step may be achieved by a chemical cleavage linearization using the periodate composition (e.g., sodium periodate) described herein.

For embodiments involving chemical cleavage linearization, it may be desirable to include P17' primer instead of P17 primer described herein. P17' primers may yield in relatively lower Read 2 error rates compared to P17 primer, for example error rates substantially similar to those of P7 primers in conjunction with enzymatic linearization. However, the reagents necessary for chemical cleavage linearization may be more cost effective than those needed for enzymatic linearization of P7 primers.

One aspect of the present disclosure relates to a method of sequencing polynucleotides, comprising:

contacting a palladium catalyst with a solid support comprising a plurality of immobilized double-stranded polynucleotides, wherein each double-stranded polynucleotides comprises a first strand and a second strand, the first strand and the second strand are immobilized to the solid support at their 5' ends, wherein the first strand comprises a first cleavage site comprising a vinyl moiety, the second strand comprises a P17' primer sequence, and the P17' primer sequence comprises a second cleavage site comprising one or more diol linkers;

cleaving one or more first strands at the first cleavage site with the palladium catalyst, to generate one or more cleaved first polynucleotides and cleaved immobilized first strands;

sequencing the immobilized second strands;

resynthesizing derivative first strands that are complementary to the second strands;

contacting a periodate salt composition with one or more second strands to cleave the second strands at the second cleavage sites to generate one or more cleaved second polynucleotides and cleaved immobilized second strands; and sequencing the immobilized derivative first strands.

In some embodiments of the sequencing method described herein, the method further comprises protecting any free 3' hydroxy group of the cleaved immobilized first strands with a 3' hydroxy protecting group prior to sequencing the immobilized second strands. In some embodiments, the method further comprises removing the one or more cleaved first polynucleotides from the solid support before sequencing the immobilized second strands. In some embodiments, the method further comprises removing the one or more cleaved second polynucleotides from the solid support before sequencing the immobilized derivative first strands. In some embodiments, the method further comprises protecting any free 3' hydroxy group of the cleaved immobilized second strands with a 3' hydroxy protecting group prior to sequencing the immobilized derivative first strands.

In some embodiments of the sequencing method described herein, the sequencing of the immobilized second strands is done through sequencing-by-synthesis (SBS), which is described in details below. In some further embodiments, the method further comprises a denature step to remove the complementary strands formed by the SBS of the immobilized second strands, before resyntheses of the immobilized derivative first strands start. In further embodiments, the method further comprises deprotecting the 3' hydroxy blocking group of the cleaved immobilized first strands before the resynthesis step. In further embodiments, the sequencing of the immobilized derivative first strands is also done through SBS.

In some embodiments of the sequencing method described herein, the first linearization reagent comprises or is a chemical linearization reagent, such as a palladium catalyst (e.g., a Pd(0) complex described herein). This step of linearization is also called the first chemical cleavage linearization. The step of the periodate salt cleavage of the diol linker at the second cleavage site is also called the second chemical cleavage linearization.

First Chemical Linearization (CCL1)

In some aspect, the palladium catalyst is an aqueous solution of a Pd complex. In some aspect, the cleavage reagent (e.g., a Pd(0) complex) is prepared in situ.

In some embodiments of the Pd catalyzed linearization method described herein, the first strands are extended from first extension primers immobilized to the solid support. In some further embodiments, the first cleavage site comprises a modified nucleoside/nucleotide that is capable of undergoing chemical cleavage by Pd(0). In some embodiments, the first cleavage site incorporating the modified nucleoside/nucleotide moiety comprises the structure of Formula (II), where the 3' oxygen of the vinyl substituted nucleoside or nucleotide is covalently attached to the 5' end of another nucleotide (structure not shown):

(II)

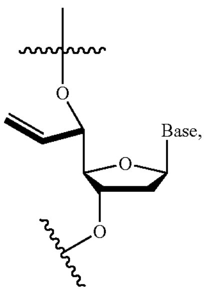

wherein Base is adenine, 7-deazaademine, guanine, 7-deazaguanine, cytosine, thymine, or uracil, or an analog or derivative thereof. In some embodiments, the modified nucleotide or nucleoside is a thymine (T) nucleoside or nucleotide analog. In further embodiment, each first extension primer comprises a P15 primer disclosed herein (SEQ ID NO. 7 or 9).

Palladium Reagents

In some embodiments of the Pd linearization methods described herein, the Pd complex used in the chemical linearization method is water soluble. In some such embodiments, the Pd complex is a Pd(0) complex. In some instances, the Pd(0) complex may be generated in situ from reduction of a Pd(II) complex by reagents such as alkenes, alcohols, amines, phosphines, or metal hydrides. Suitable palladium sources include $Na_2PdCl_4$, $Li_2PdCl_4$, $Pd(CH_3CN)_2Cl_2$, $(PdCl(C_3H_5))_2$, $[Pd(C_3H_5)(THP)]Cl$, $[Pd(C_3H_5)(THP)_2]Cl$, $Pd(OAc)_2$, $Pd(Ph_3)_4$, $Pd(dba)_2$, $Pd(Acac)_2$, $PdCl_2(COD)$, $Pd(TFA)_2$, $Na_2PdBr_4$, $K_2PdBr_4$, $PdCl_2$, $PdBr_2$, and $Pd(NO_3)_2$. In one such embodiment, the Pd(0) complex is generated in situ from $Na_2PdCl_4$ or $K_2PdCl_4$In another embodiment, the palladium source is allyl palladium(II) chloride dimer $[(PdCl(C_3H_5))_2]$. In some embodiments, the Pd(0) complex is generated in an aqueous solution by mixing a Pd(II) complex with a phosphine. Suitable phosphines include water soluble phosphines, such as tris(hydroxypropyl)phosphine (THP), tris(hydroxymethyl)phosphine (THM), 1,3,5-triaza-7-phosphaadamantane (PTA), bis (p-sulfonatophenyl)phenylphosphine dihydrate potassium salt, tris(carboxyethyl)phosphine (TCEP), and triphenylphosphine-3,3',3"-trisulfonic acid trisodium salt.

In some embodiments, the Pd complex is a Pd(II) complex (e.g., $Pd(OAc)_2$, $[(Allyl)PdCl]_2$, $Na_2PdCl_4$ or $K_2PdCl_4$), which generates Pd(0) in situ in the presence of the phosphine (e.g., THP). The molar ratio of $[(Allyl)PdCl]_2$ and the THP may be about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5 or 1:10. In one embodiment, the molar ratio of $[(Allyl)PdCl]_2$ to THP is 1:10. In some other embodiment, the palladium catalyst is prepared by mixing a water soluble Pd reagent such as $Na_2PdCl_4$ or $K_2PdCl_4$ with THP in situ. The molar ratio of $Na_2PdCl_4$ or $K_2PdCl_4$ and THP may be about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5 or 1:10. In one embodiment, the molar ratio of $Na_2PdCl_4$ or $K_2PdCl_4$ to THP is about 1:3. In another embodiment, the molar ratio of $Na_2PdCl_4$ or $K_2PdCl_4$ to THP is about 1:3.5. In yet another embodiment, the molar ratio of $Na_2PdCl_4$ or $K_2PdCl_4$ to THP is about 1:2.5. In some further embodiments, one or more reducing agents may be added, such as ascorbic acid or a salt thereof (e.g., sodium ascorbate). In some other embodiments, the Pd(0) is prepared by mixing a Pd(II) pre-catalyst such as $[Pd(C_3H_5)(THP)]Cl$, $[Pd(C_3H_5)(THP)_2]Cl$ with additional THP. $[Pd(C_3H_5)(THP)]Cl$ and $[Pd(C_3H_5)(THP)_2]Cl$ may be prepared by reacting $(PdCl(C_3H_5))_2$ with 1 to 5 equivalents of THP and they may be isolated prior to use in the chemical linearization reaction.

Second Chemical Linearization (CCL2)

In some embodiments of the sequencing method described herein, the cleavages site of the P17' primer comprises at least two diol linker moieties, or three linker moieties. In some embodiments, the diol linker comprises a structure of Formula (I):

(I)

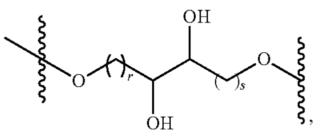

wherein r is 2, 3, 4, 5, or 6; and s is 2, 3, 4, 5, or 6. In one embodiment, the diol linker comprises a structure of Formula (Ia):

(Ia)

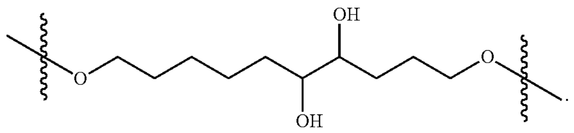

In further embodiments, the second strands are extended from second extension primers immobilized to the solid support, and wherein each second extension primer comprises a P17' sequence.

In other embodiments, the first cleavage site may be cleaved by a method selected from the group consisting of photo cleavage, enzymatic cleavage, or a combination thereof. In one embodiment, the first cleavage site may be cleaved by an enzymatic cleavage reaction. In one embodiment, the first extension primer is a P5 primer disclosed herein (SEQ ID NO. 1 or 3), containing a deoxyuridine (U) that can be enzymatically cleaved by enzyme USER.

In any embodiments of the sequencing method described herein, the P17' primer sequence comprises SEQ ID NO. 11.

Denaturation

In any embodiments of method used for cleavage, the product of the cleavage reaction may be subjected to denaturing conditions in order to remove the portion(s) of the cleaved strand(s) that are not attached to the solid support. Suitable denaturing conditions will be apparent to the skilled reader with reference to standard molecular biology protocols (Sambrook et al., 2001, Molecular Cloning, A Laboratory Manual, 3rd Ed, Cold Spring Harbor Laboratory Press, Cold Spring Harbor Laboratory Press, NY; Current Protocols, eds., Ausubel et al.). Denaturation (and subsequent re-annealing of the cleaved strands) results in the production of a sequencing template which is partially or substantially single-stranded. A sequencing reaction may then be initiated by hybridization of a sequencing primer to the single-stranded portion of the template.

In other embodiments, sequencing can be initiated directly after the cleavage step with no need for denaturation to remove a portion of the cleaved strand(s). If the cleavage step generates a free 3' hydroxyl group on one cleaved strand still hybridized to a complementary strand, then sequencing can proceed from this point using a strand-displacement polymerase enzyme without the need for an initial denaturation step. In particular, strand displacement sequencing may be used in conjunction with template generation by cleavage with nicking endonucleases, or by hydrolysis of an abasic site with endonuclease, heat or alkali treatment.

Methods of Reducing Read 2 Error Rates

In pair-end SBS using a first and a second extension primer (e.g., P15/P17 primer set described herein), it has been observed that the percent mismatch rate (% MMR) in Read 2 was higher than that of the SBS using P5/P7 primer set or P15/P7 primer set. For example, the Read 2% MMR for P15/P7 may range from 0.5 to 0.6, or 0.51 to 0.59, while the Read 2% MMR for P15/P17 ranges from 0.8 to 0.9, or 0.81 to 0.89. The present disclosure provides alternative P17' primer where one or more diol linker moieties are closer to the 5' end of the sequence than the P17 primer. In other words, the diol linkers are closer to the surface of the solid support. In particular, the diol linker(s) may be attached to the surface without any intervening nucleotides, or the diol linker(s) may be in a position that is within 1, 2, 3, or 4 nucleotides from the 5' end.

Another aspect of the present disclosure relates to a method of reducing sequencing by synthesis error rate, comprising:

- contacting a solid support comprising a plurality of immobilized double-stranded polynucleotides with a first cleavage reagent, wherein each double-stranded polynucleotides comprises a first strand and a second strand, the first strand and the second strand are immobilized to the solid support at their 5' ends, wherein the first strand comprises a first cleavage site capable of being cleaved by the first cleavage reagent, the second strand comprises a P17' primer sequence, and the P17' primer sequence comprises a second cleavage site comprising one or more diol linkers;
- cleaving one or more first strands at the first cleavage site with the first cleavage reagent to generate one or more cleaved first polynucleotides and cleaved immobilized first strands;
- performing a first run of sequencing of the immobilized second strands;
- resynthesizing derivative first strands that are complementary to the second strands;
- contacting a periodate salt composition with one or more second strands to cleave the second strands at the second cleavage sites to generate one or more cleaved second polynucleotides and cleaved immobilized second strands; and
- performing a second round of sequencing of the immobilized derivative first strands;
- wherein the method results in at least about 5% reduction in the second round of sequencing error rate relative to methods wherein the second strand comprises a P17 primer sequence.

In some embodiments of the method described herein, the method further comprises protecting any free 3' hydroxy group of the cleaved immobilized first strands with a 3' hydroxy protecting group prior to sequencing the immobilized second strands. In some embodiments, the method further comprises removing the one or more cleaved first polynucleotides from the solid support before sequencing the immobilized second strands. In some embodiments, the method further comprises removing the one or more cleaved second polynucleotides from the solid support before sequencing the immobilized derivative first strands. In some embodiments, the method further comprises protecting any free 3' hydroxy group of the cleaved immobilized second strands with a 3' hydroxy protecting group prior to sequencing the immobilized derivative first strands.

In some embodiments of the method described herein, the sequencing of the immobilized second strands is done through sequencing-by-synthesis (SBS), which is described in detail below. In some further embodiments, the method further comprises a denature step to remove the complementary strands formed by the SBS of the immobilized second strands, before resyntheses of the immobilized derivative first strands start. In further embodiments, the method further comprises deprotecting the 3' hydroxy protecting group of the cleaved immobilized first strands before the resynthesis step. In further embodiments, the sequencing of the immobilized derivative first strands is also done through SBS.

In some embodiments of the reducing error method described herein, first cleavage reagent comprises a palladium catalyst, for example a Pd(0) catalyst described herein. In further embodiments, wherein the first cleavage site comprises a modified nucleotide comprising a structure of Formula (II):

(II)

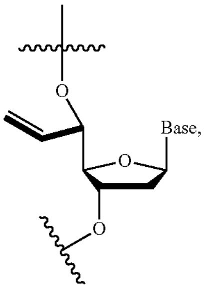

wherein Base is adenine, 7-deazaademine, guanine, 7-deazaguanine, cytosine, thymine, or uracil, or a derivative thereof. In further embodiments, the first strands are extended from first extension primers immobilized to the solid support, and wherein the first extension primer comprises a P15 sequence. In some embodiments, the cleavages site of the P17' primer comprises at least two diol linker moieties, or three linker moieties. In further embodiments, the diol linker moiety comprises a structure of Formula (I):

(I)

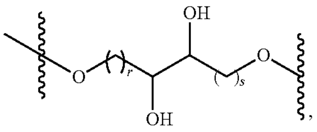

wherein r is 2, 3, 4, 5, or 6; and s is 2, 3, 4, 5, or 6. In one embodiment, the diol linker comprises a structure of Formula (Ia):

(Ia)

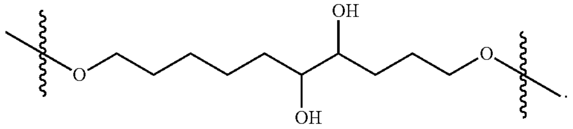

In further embodiments, the second strands are extended from second extension primers immobilized to the solid support, and wherein the second extension primer comprises the P17' sequence.

In other embodiments, the first cleavage site may be cleaved by a method selected from the group consisting of photo cleavage, enzymatic cleavage, or a combination thereof. In one embodiment, the first cleavage site may be cleaved by an enzymatic cleavage reaction. In one embodiment, the first extension primer is a P5 primer disclosed herein, containing a deoxyuridine (U) that can be enzymatically cleaved by enzyme USER.

In any embodiments of the method for reducing Read 2 error rate, the P17' primer sequence comprises SEQ ID NO. 11. In further embodiments, the Read 2 error rate include percent mismatch rate (% MMR). In further embodiments, the method results in at least about 5%, 10%, 15%, 20%, 25%, 30%, 35%, 40%, 45%, or 50% reduction in the second round of sequencing error rate relative to methods wherein the second strand comprises a P17 primer sequence.

Periodate Compositions for Diol Cleavage

In any embodiments of the method described herein, the cleavage reagent for cleaving the diol linker is a periodate salt composition, comprising a periodate salt, and at least one ionic liquid additive, wherein when the composition forms an aqueous solution, the periodate salt does not form a precipitate in the aqueous solution. As described herein, when a precipitate is not form, it means the precipitate cannot be observed in the aqueous solution. In further embodiments, the precipitate is not formed after the composition is subject to at least 2, 3, 4, 5, 6, 7, 8, 9, 10, 15 or 20 freeze/thaw cycles. In further embodiments, the precipitate may be less than 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.005%, or 0.001% by weight of the total amount of periodate salt in the composition.

In some embodiments of the composition described herein, the concentration of the periodate salt in the composition is from about 0.1 mM to about 300 mM, from about 0.5 mM to about 200 mM, from about 1 mM to about 150 mM, from about 2 mM to about 100 mM, or from about 5 mM to about 50 mM. In further embodiments, the concentration of the periodate salt in the composition is about 1 mM, 2 mM, 3 mM, 4 mM, 5 mM, 6 mM, 7 mM, 8 mM, 9 mM, 10 mM, 12 mM, 14 mM, 16 mM, 18 mM, 20 mM, or 25 mM, or a range defined by any two of the preceding values. In one embodiment, the concentration of the periodate salt in the composition is about 10 mM. In another embodiment, the concentration of the periodate salt in the composition is about 25 mM.

In some embodiments of the composition or method described herein, the ionic liquid additive comprises or is selected from the group consisting of a crown ether or a substituted imidazolium salt, or a combination thereof. In some such embodiments, the crown ether comprises or is 15-crown-S. In some embodiments, the molar ratio of 15-crown-5 to the periodate salt in the composition is from about 1:1 to about 50:1, from about 5:1 to about 25:1, or about 10:1.

In some other embodiments of the composition or method described herein, the composition comprises a substituted imidazolium salt, for example, 1-benzyl-3-methylimidazolium chloride ([Bzmim]Cl having the structure

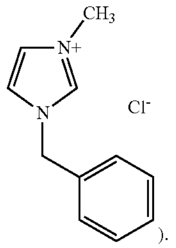

In some such embodiments, the molar ratio of [Bzmim]Cl to the periodate salt in the composition is from about 1:1 to about 100:1, from about 5:1 to about 75:1, or from about 10:1 to about 50:1. In further embodiments, the molar ratio of [Bzmim]Cl to the periodate salt is about 5:1, 10:1, 15:1, 20:1, 25:1, 30:1, 35:1, 40:1, 45:1 or 50:1, or a range defined by any two of the preceding values. In one embodiment, the molar ratio of [Bzmim]Cl to the periodate salt is about 30:1. In some embodiments, the addition of [Bzmim]Cl increased the periodate linearization activity, when compared to using the same periodate solution without [Bzmim]Cl. For example, the linearization rate with the addition of [Bzmim]Cl may increase at least 10%, 20%, 30%, 40%, 50%, 60%, 70%, 80%, 90%, 100%, 150%, 200%, 250%, 300%, 350%, 400%, 450% or 500%, when compared to the periodate composition without [Bzmim]Cl.

In some embodiments of the composition or method described herein, the composition comprises one or more inorganic salts. The presence of these inorganic salts may increase the ionic strength of the composition, and results in an increased linearization rate. For example, the inorganic salt may comprise one or more sodium salts, or one or more magnesium salts, or a combination thereof. In further embodiments, the inorganic salt may comprise sodium citrate, sodium acetate, sodium chloride, magnesium sulfate, or combinations thereof.

In some embodiments of the composition or method described herein, the pH of the composition is from about 4 to about 8, about 5 to about 7.5, or about 6. In one embodiment, the pH of the composition is about 5.2. In another embodiment, the pH of the composition is about 6.0.

In any embodiments of the composition or method described herein, the periodate salt comprises or is sodium periodate.

Solid Support

A further aspect of the present disclosure relates to a solid support comprising:

a plurality of immobilized first extension primers; and
a plurality of immobilized second extension primers;
wherein both the first extension primers and the second extension primers are immobilized at their 5' ends;
the first extension primers each comprises a first cleavage site; and
the second extension primers each comprises a P17' primer sequence comprising one or more diol linkers.

In some embodiments, the first cleavage site of the first extension primers is cleavable by a palladium complex (e.g., Pd(0) catalyst). In further embodiments, the first extension primer comprises a P15 primer sequence. In further embodiments, the palladium complex is generated in situ from a palladium (II) complex $Na_2PdCl_4$, $K_2PdCl_4$ or $(PdAllylCl)_2$ in the presence of THP.

In further embodiments, the solid support comprises a plurality of different double-stranded polynucleotides, and each double-stranded polynucleotides comprises a first strand and a second strand, wherein the first strands are extended from the first extension primers and the second strands are extended from the second extension primers.

In some embodiments, the first and the second strand polynucleotides are immobilized on the solid support through covalent bonding with a polymer or hydrogel coating on a surface of the solid support. In some further embodiments, the polymer or hydrogel coating comprises PAZAM.

In some embodiments, the solid support is a patterned solid support with a planar patterned surface. For example, the solid support may comprise or is a flow cell. In further embodiments, the solid support (flow cell) comprises a patterned array of a plurality of different double-stranded polynucleotides, and each double-stranded polynucleotides comprises a first strand and a second strand, wherein the first strands are extended from the first extension primers and the second strands are extended from the second extension primers, the first extension primer comprises a P15 sequence described herein, and the second extension primer comprises a P17' primer described herein.

In any embodiments of the solid support, the P17' primer sequence comprises SEQ ID NO. 11.

Sequencing by Synthesis

In some embodiments, the methods described herein can be used for determining a nucleotide sequence of a polynucleotide. In such embodiments, the method can comprise the steps of (a) contacting a polynucleotide polymerase with delinearized polynucleotide (also described below as target polynucleotide) clusters attached to a surface of a substrate (e.g., via any one of the polymer or gel coatings described herein); (b) providing nucleotides to the surface of the substrate such that a detectable signal is generated when one or more nucleotides are utilized by the polynucleotide polymerase; (c) detecting signals at one or more attached polynucleotide (or one or more clusters produced from the attached polynucleotides); and (d) repeating steps (b) and (c), thereby determining a nucleotide sequence of a substrate-attached polynucleotide.

Labeled nucleotides may be used in any method of analysis such as method that include detection of a fluorescent label attached to such nucleotide, whether on its own or incorporated into or associated with a larger molecular structure or conjugate. In this context the term "incorporated into a polynucleotide" can mean that the 5' phosphate is joined in phosphodiester linkage to the 3' hydroxyl group of a second nucleotide, which may itself form part of a longer polynucleotide chain. The 3' end of a nucleotide set forth herein may or may not be joined in phosphodiester linkage to the 5' phosphate of a further nucleotide. Thus, in one non-limiting embodiment, the disclosure provides a method of detecting a labeled nucleotide incorporated into a polynucleotide which comprises: (a) incorporating at least one labeled nucleotide of the disclosure into a polynucleotide and (b) determining the identity of the nucleotide(s) incorporated into the polynucleotide by detecting the fluorescent signal from the dye compound attached to said nucleotide(s).

This method can include: a synthetic step (a) in which one or more labeled nucleotides according to the disclosure are incorporated into a single stranded polynucleotide and a detection step (b) in which one or more labeled nucleotide(s) incorporated into the polynucleotide are detected by detecting or quantitatively measuring their fluorescence.

Some embodiments of the present application are directed to a method of determining the sequence of a plurality of different target polynucleotides (e.g., single-stranded target polynucleotides), comprising:

(a) contacting a solid support with a solution comprising sequencing primers under hybridization conditions, wherein the solid support comprises a plurality of different target polynucleotides immobilized thereon; and the sequencing primers are complementary to at least a portion of the target polynucleotides;
(b) contacting the solid support with an aqueous solution comprising DNA polymerase and one more of four different types of nucleotides (e.g., dATP, dGTP, dCTP and dTTP or dUTP), under conditions suitable for DNA polymerase-mediated primer extension, and incorporating one type of nucleotides into the sequencing primers to produce extended copy polynucleotides, wherein at least one type of nucleotide is a chromenoquinoline labeled nucleotide described herein, and wherein each of the four types of nucleotides comprises a 3' blocking group;
(c) imaging the solid support and performing one or more fluorescent measurements of the extended copy polynucleotides; and
(d) removing the 3' blocking group of the incorporated nucleotides. In some embodiments, step (d) also removes the labels of the incorporated nucleotides (if the incorporated nucleotides are labeled). In some such embodiments, the labels and the 3' blocking groups of the incorporated nucleotides are removed in a single chemical reaction. In some further embodiments, the method may also comprises (e) washing the solid support with an aqueous wash solution (e.g., washing the removed label moiety and the 3' blocking group away from the extended copy polynucleotides). In some embodiments, steps (b) through (e) are repeated at least 30, 40, 50, 60, 70, 80, 90, 100, 110, 120, 130, 140, 150, 160, 170, 180, 190, 200, 250, 300, 350, 400, 450 or 500 cycles to determine the target polynucleotide sequences. In some further embodiments, the method is performed on an automated sequencing instrument, and wherein the automated sequencing instrument comprises two light sources operating at different wavelengths, or a single light source. In some embodiments, the four types of nucleotides comprise dATP, dCTP, dGTP and dTTP or dUTP, or non-natural nucleotide analogs thereof. In some embodiments, the sequence determination is conducted after the completion of repeated cycles of the sequencing steps described herein.

In some embodiments, at least one nucleotide is incorporated into a polynucleotide (such as a single stranded primer polynucleotide described herein) in the synthetic step by the action of a polymerase enzyme. However, other methods of joining nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template or target polynucleotide strand with a reaction mixture comprising fluorescently labeled nucleotides of the disclosure. A polymerase can also be provided under conditions which permit formation of a phosphodiester linkage between a free 3' hydroxyl group on a polynucleotide strand annealed to the template or target polynucleotide strand and a 5' phosphate group on the labeled nucleotide. Thus, a synthetic step can include formation of a polynucleotide strand as directed by complementary base pairing of nucleotides to a template/target strand.

In all embodiments of the methods, the detection step may be carried out while the polynucleotide strand into which the labeled nucleotides are incorporated is annealed to a template/target strand, or after a denaturation step in which the two strands are separated. Further steps, for example chemical or enzymatic reaction steps or purification steps, may be included between the synthetic step and the detection step. In particular, the polynucleotide strand incorporating the labeled nucleotide(s) may be isolated or purified and then processed further or used in a subsequent analysis. By way of example, polynucleotide strand incorporating the labeled nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including the labeled nucleotides as described herein, to form an extended polynucleotide strand (primer polynucleotide strand) complementary to the template/target strand in the presence of a suitable polymerase enzyme. In other embodiments, the synthetic step may itself form part of an amplification reaction producing a labeled double stranded amplification product comprised of annealed complementary strands derived from copying of the primer and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of the labeled nucleotides as set forth herein. A variety of naturally occurring or mutant/modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the labeled nucleotides according to the disclosure include those described in WO 2005/024010, WO06120433, U.S. Publication Nos. 2020/0131484 A1, 2020/0181587 A1, and U.S. Ser. Nos. 63/412,241 and 63/433,971, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the modified nucleotide or nucleoside labeled with dyes set forth herein when incorporated into a polynucleotide.

A particular embodiment of the disclosure provides use of labeled nucleotides comprising dye moiety according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template/target nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the nucleotides labeled with dyes set forth herein for determination of the identity of a single base may be useful, for example, in the scoring of single nucleotide polymorphisms, and such single base extension reactions are within the scope of this disclosure.

In an embodiment of the present disclosure, the sequence of a template/target polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template/target polynucleotide, and the blocking group prevents further incorporation of nucleotides. Any unincorporated nucleotides can be washed away and the fluorescent signal from each incorporated nucleotide can be "read" optically by suitable means, such as a charge-coupled device using light source excitation and suitable emission filters. The 3' blocking group and fluorescent dye compounds can then be removed (deprotected) (simultaneously or sequentially) to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group that serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments, sequencing may proceed by strand displacement. In certain embodiments, a primer bearing the free 3' hydroxyl group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO0157248 and WO2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to a support (for example, silica-based supports such as those disclosed in WO00/06770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO2005/047301 (incorporated herein by reference). A still further example of solid-supported template polynucleotides is where the template polynucleotides are attached to hydrogel supported upon silica-based or other solid supports, for example, as described in WO00/31148, WO01/01143, WO02/12566, WO03/014392, U.S. Pat. No. 6,465,178 and WO00/53812, each of which is incorporated herein by reference.

A particular surface to which template polynucleotides may be immobilized is a polyacrylamide hydrogel. Polyacrylamide hydrogels are described in the references cited above and in WO2005/065814, which is incorporated herein by reference. Specific hydrogels that may be used include those described in WO2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in Nature, 437, 376-380 (2005); Science, 309, 5741, 1728-1732 (2005), each of which is incorporated herein by reference. Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high-density arrays, including single-molecule arrays, clustered arrays, and bead arrays. Nucleotides labeled with dye compounds of the present disclosure may be used for sequencing templates on essentially any type of array, including but not limited to those formed by immobilization of nucleic acid molecules on a solid support.

However, nucleotides labeled with dye compounds of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using nucleotides labeled with dye compounds of the disclosure.

Nucleotides labeled with dye compounds of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO 00/06770 and WO 01/57248, each of which is incorporated herein by reference. Although one use of the labeled nucleotides of the disclosure is in sequencing-by-synthesis reactions, the utility of such nucleotides is not limited to such methods. In fact, the labeled nucleotides described herein may be used advantageously in any sequencing methodology which requires detection of fluorescent labels attached to nucleotides incorporated into a polynucleotide.

In particular, nucleotides labeled with dye compounds of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods and related protocols (Sanger-type) utilize randomized chain termination with labeled dideoxynucleotides.

Thus, the present disclosure also encompasses nucleotides labeled with dye compounds which are dideoxynucleotides lacking hydroxyl groups at both of the 3' and 2' positions, such modified dideoxynucleotides being suitable for use in Sanger type sequencing methods and the like.

Nucleotides labeled with dye compounds of the present disclosure incorporating 3' blocking groups, it will be recognized, may also be of utility in Sanger methods and related protocols since the same effect achieved by using dideoxy nucleotides may be achieved by using nucleotides having 3' OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

Alternatively, the sequencing methods described herein may also be carried out using unlabeled nucleotides and affinity reagents containing a fluorescent dye described herein. For example, one, two, three or each of the four different types of nucleotides (e.g., dATP, dCTP, dGTP and dTTP or dUTP) in the incorporation mixture of step (a) may be unlabeled. Each of the four types of nucleotides (e.g., dNTPs) has a 3' hydroxyl blocking group to ensure that only a single base can be added by a polymerase to the 3' end of the primer polynucleotide. After incorporation of an unlabeled nucleotide in step (b), the remaining unincorporated nucleotides are washed away. An affinity reagent is then introduced that specifically recognizes and binds to the incorporated dNTP to provide a labeled extension product comprising the incorporated dNTP. Uses of unlabeled nucleotides and affinity reagents in sequencing-by-synthesis have been disclosed in WO 2018/129214 and WO 2020/097607. A modified sequencing method of the present disclosure using unlabeled nucleotides may include the following steps:

(a') contacting a solid support with a solution comprising sequencing primers under hybridization conditions, wherein the solid support comprises a plurality of different target polynucleotides immobilized thereon; and the sequencing primers are complementary to at least a portion of the target polynucleotides;

(b') contacting the solid support with an aqueous solution comprising DNA polymerase and one more of four different types of unlabeled nucleotides (e.g., dATP, dCTP, dGTP, and dTTP or dUTP) under conditions suitable for DNA polymerase-mediated primer extension, and incorporating one type of nucleotides into the sequencing primers to produce extended copy polynucleotides, and wherein each of the four types of nucleotides comprises a 3' blocking group;

(c') contacting the extended copy polynucleotides with a set of affinity reagents under conditions wherein one affinity reagent binds specifically to the incorporated unlabeled nucleotides to provide labeled extended copy polynucleotides;

(d') imaging the solid support and performing one or more fluorescent measurements of the extended copy polynucleotides; and (e') removing the 3' blocking group of the incorporated nucleotides.

In some embodiments of the modified sequencing method described herein, the method further comprises removing the affinity reagents from the incorporated nucleotides. In still further embodiments, the 3' blocking group and the affinity reagent are removed in the same reaction. In some embodiments, the method further comprises a step (f') washing the solid support with an aqueous wash solution. In further embodiments, steps (b') through (f') are repeated at least 50, 100, 150, 200, 250, 300, 350, 400, 450 or 500 cycles to determine the target polynucleotide sequences. In some embodiments, the set of affinity reagents may comprise a first affinity reagent that binds specifically to the first type of nucleotide, a second affinity reagent that binds specifically to the second type of nucleotide, and a third affinity reagent that binds specifically to the third type of nucleotide. In some further embodiments, each of the first, second and the third affinity reagents comprises a detectable labeled that is spectrally distinguishable. In some embodiments, the affinity reagents may include protein tags, antibodies (including but not limited to binding fragments of antibodies, single chain antibodies, bispecific antibodies, and the like), aptamers, knottins, affimers, or any other known agent that binds an incorporated nucleotide with a suitable specificity and affinity. In one embodiment, at least one affinity reagent is an antibody or a protein tag. In another embodiment, at least one of the first type, the second type, and the third type of affinity reagents is an antibody or a protein tag comprising one or more detectable labels (e.g., multiple copies of the same detectable label).

EXAMPLES

Additional embodiments are disclosed in further detail in the following examples, which are not in any way intended to limit the scope of the claims.

Example 1. Measurement of P17' Read 2 Error Rates with Various Periodate Compositions A P17' primer set forth in SEQ ID NO. 11 was assessed to determine performance of the second cluster chemical linearization (CCL2) when used with various periodate compositions. Specifically, Read 2 error rate (% MMR) was assessed in three different periodate compositions: (1) 10 mM sodium periodate, (2) 10 mM sodium periodate with 100 mM 15-crown-5, and (3) 10 mM sodium periodate with 304 mM Bzmim Cl. S4 flowcells (Illumina) were prepared. The primers (e.g., P15/P17') were grafted onto lanes within each test flowcell. Additionally, flowcells having P15/P7 primers were run as a control. Flowcells were run on the HiSeq® X (Illumina) with the following sequencing conditions: PCR free 450, PhiX spike-in (150 pm loading), 2×151 cycles.

Figure 2:
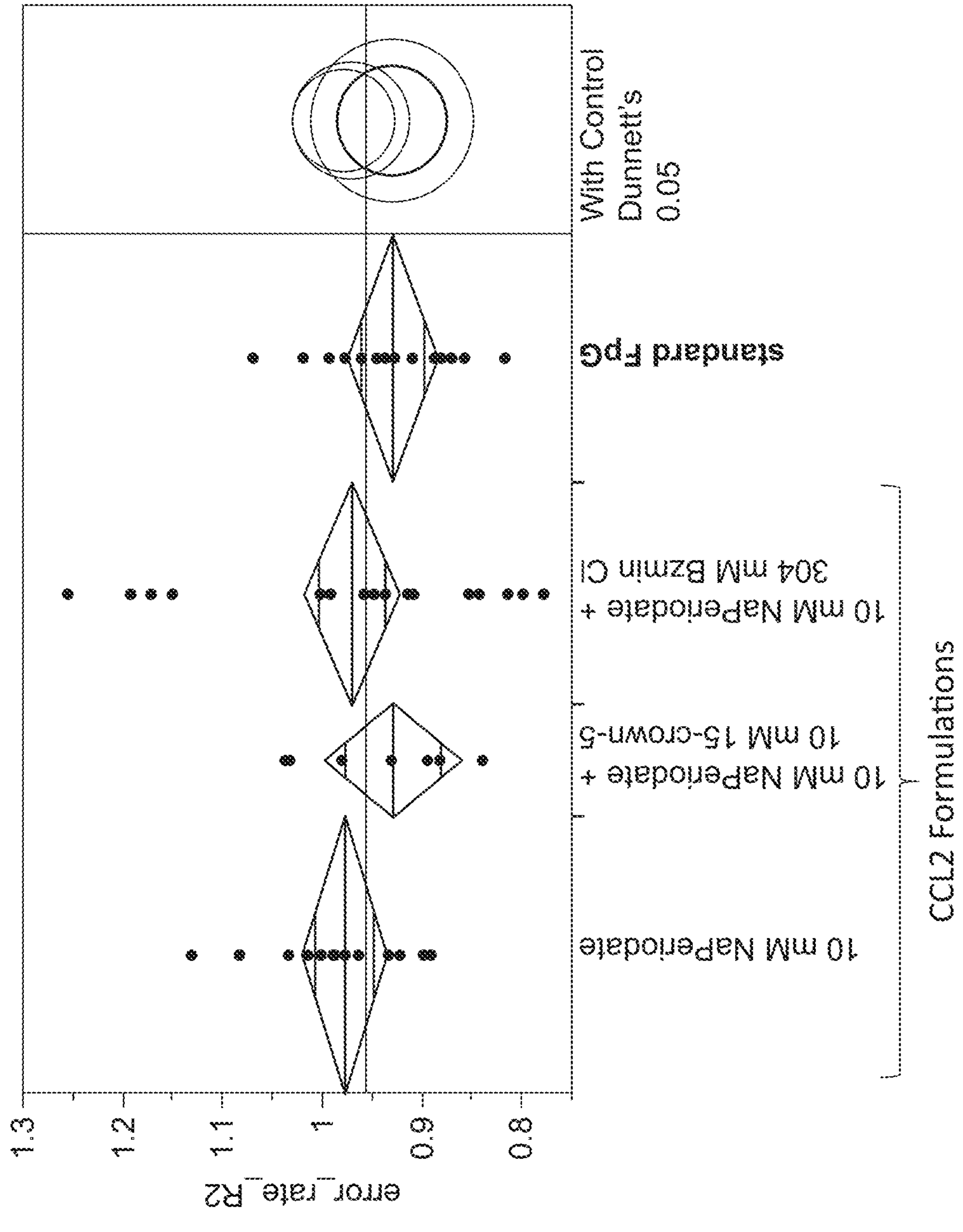
FIG. 2 illustrates Read 2 error rates of flow cell lanes grafted with P15 and P17' primers in the presence of various periodate cleaving formulations.

FIG. 2 shows Read 2 error rates for each periodate compositions and the enzymatic Read 2 control (standard FpG). Each data point represents Read 2 error rate of a single lane from a flow cell. None of the three formulations had Read 2 error rates significantly different than that of the enzymatic control using Dunnett's multiple comparison test at p=0.05.

Example 2. Comparison of P17' and P7 Read 2 Error Rates

A P17' primer set forth in SEQ ID NO. 11 was assessed the in the context of a linearization workflow on a NovaSeg™ system (Illumina). The goal was to compare a CCL2 P17' primer workflow to an enzymatic linearization process involving P7 primers. A full chemical linearization workflow (wherein both R1 and R2 linearization formulations were chemical formulations through use of P15/P17' primers) with partial ("half") chemical/enzymatic linearization options that included of one chemical linearization step and one enzymatic linearization step (wherein the R1 linearization was a chemical formulation but R2 linearization was an enzymatic formulation by using P15/P7 primers).

S4 flowcells (Illumina) were prepared. The primers for each condition were grafted onto lanes within each flowcell. Lanes 1 and 2, the CCL lanes, were grafted with P15/P17' primers while lanes 3 and 4, the enzyme lanes, were grafted with the P15/P7 primers.

First, the library was titrated to determine a suitable library concentration for each lane. Lanes 1 and 3 were loaded with 40 pM of library DNA whereas Lanes 2 and 4 were loaded with 60 pM of library DNA. For the linearization step, the CCL lanes were given 10 mM Na periodate and 304 mM Bzmim Cl, while the enzymatic lanes were given 0.4 μM of enzyme.

Lanes 1 and 2 produced Read 1 and Read 2 signal about 20-25% more intense than that of lanes 3 and 4. DNA library loading concentration did not correlate with this increase in intensity (i.e., signal from Lane 1, which had P15/P17' primers but only 40 pM of DNA loaded, was more intense than signal from Lane 4, which had P15/P7 primers and 60 pM of DNA loaded). Based in part on the relatively low % pass filter and % occupied metrics of lane 3 (P7 primer with 40 pM library concentration), a library concentration of 60 pM was chosen for subsequent comparison.

Lanes were run again at a library loading concentration of 60 pM across all lanes. For the linearization step, the CCL lanes were given 10 mM sodium periodate and 304 mM Bzmim Cl, while the enzymatic lanes were given 0.4 μM of enzyme. The Read 2 error rate for the CCL lanes were 0.74% whereas the Read 2 error rate for the enzyme lanes was 0.77%. This difference was significant using the Tukey-Kramer test at p=0.05.

What is claimed is:

1. A method of linearizing a plurality of immobilized double-stranded polynucleotides, comprising:

contacting a solid support comprising a plurality of immobilized double-stranded polynucleotides with a periodate salt composition, wherein each of the double-stranded polynucleotides comprises a first strand and a second strand, the first strand and the second strand are immobilized to the solid support at their 5' ends, and the second strand comprises a P17' primer sequence at the 5' end of the second strand, and wherein the P17' primer sequence comprises a cleavage site having one or more diol linkers, and wherein the P17' primer comprises a sequence of any one of SEQ ID Nos. 11-25; and cleaving one or more second strands at the cleavage site with the periodate salt, and generating one or more cleaved second polynucleotides.

2. The method of claim 1, wherein the P17' primer sequence comprises SEQ ID NO. 11.

3. The method of claim 1, further comprising removing the cleaved second polynucleotides from the solid support.

4. The method of claim 1, wherein the cleavage site of each second strand comprises at least two diol linkers.

5. The method of claim 4, wherein the diol linker comprises a structure of Formula (I):

(I)

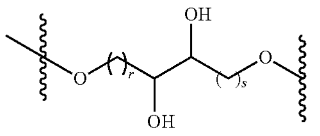

wherein r is 2, 3, 4, 5, or 6; and s is 2, 3, 4, 5, or 6.

6. The method of claim 5, wherein the diol linker comprises a structure of Formula (Ia):

(Ia)

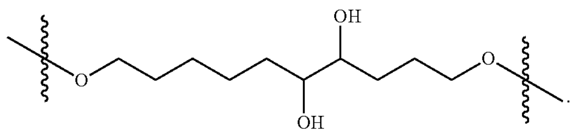

7. The method of claim 1, wherein the periodate salt composition is an aqueous solution comprising the periodate salt and at least one ionic liquid additive, and wherein the periodate salt does not form a precipitate in the aqueous solution.

8. The method of claim 7, wherein the concentration of the periodate salt in the composition is from about 0.1 mM to about 300 mM.

9. The method of claim 8, wherein the concentration of the periodate salt in the composition is about 10 mM to about 25 mM.

10. The method of claim 9, wherein the molar ratio of the ionic liquid additive to the periodate salt is from about 1:1 to about 100:1.

11. The method of claim 10, wherein the molar ratio of the ionic liquid additive to the periodate salt in the composition is about 30:1.

12. The method of claim 7, wherein the ionic liquid additive comprises or is 1-benzyl-3-methylimidazolium chloride ([Bzmim]Cl).

13. The method of claim 7, wherein the periodate salt composition further comprises one or more inorganic salts.

14. The method of claim 13, wherein the inorganic salt comprises sodium citrate, sodium acetate, magnesium sulfate, or combinations thereof.

15. The method of claim 7, wherein the pH of the periodate composition is from about 4 to about 8.

16. The method of claim 15, wherein the pH of the periodate composition is from about 5.5 to about 6.

17. The method of claim 7, wherein no precipitate of the periodate salt is formed after the periodate composition is subject to at least 5 freeze/thaw cycles.

18. The method of claim 15, wherein the pH of the periodate composition is from about 5 to about 7.5.

19. The method of claim 10, wherein the molar ratio of the ionic liquid additive to the periodate salt is from about 10:1 to about 50:1.

20. The method of claim 8, wherein the concentration of the periodate salt in the composition is from about 0.5 mM to about 200 mM.

* * * * *